United States Patent [19]
Yamada

[11] Patent Number: 5,828,058
[45] Date of Patent: Oct. 27, 1998

[54] OPTICAL FIBER REMOTE SENSING SYSTEM WITH ELECTROMAGNETIC WAVE MEASUREMENT

[75] Inventor: Hirohito Yamada, Tokyo, Japan

[73] Assignee: NEC Corporation, Tokyo, Japan

[21] Appl. No.: 856,978

[22] Filed: May 15, 1997

[30] Foreign Application Priority Data

May 15, 1996 [JP] Japan ................................. 8-120438

[51] Int. Cl.[6] ....................................... H01J 5/16
[52] U.S. Cl. ................................. 250/227.14; 356/437
[58] Field of Search ...................... 250/227.11, 227.14, 250/227.23; 336/437, 438; 342/124, 125; 343/703

[56] References Cited

U.S. PATENT DOCUMENTS 3,860,818 1/1975 Stalder et al. ......................... 356/437

OTHER PUBLICATIONS

Uetaki, M., "Millimeter Wave Technique Manual and Development", Realize Co., Jun. 30, 1993, p. 156.

Primary Examiner—Que Le
Attorney, Agent, or Firm—Foley & Lardner

[57] ABSTRACT

Disclosed is an optical fiber remote sensing system, which has: first and second light sources which are connected to ends of branched optical fibers and emit lights with two wavelengths different from each other; one or more optical detectors which conduct a photoelectric conversion of the lights propagated through the optical fibers from the first and second light sources and generate an electromagnetic wave with a wavelength corresponding to a difference between the two different wavelengths; and a measuring means which receives the electromagnetic wave propagated through a measured substance and measures a state of the measured substance based on an optical absorption characteristic of the measured substance.

5 Claims, 3 Drawing Sheets

5,828,058

OPTICAL FIBER REMOTE SENSING SYSTEM WITH ELECTROMAGNETIC WAVE MEASUREMENT

FIELD OF THE INVENTION

This invention relates to an optical fiber remote sensing system, and more particularly to, an optical fiber remote sensing system used in various remote sensing uses, such as a remote leakage detection of an explosive gas, toxic gas etc., a remote measurement of air pollution and a remote measurement of rainfall.

BACKGROUND OF THE INVENTION

An conventional optical fiber remote sensing system comprises a laser light source which emits a light in near infrared region or visible region, and optical fiber through which the light is propagated at a low loss, a gas detection cell which is located at a measuring point and into which the light is led through the optical fiber, an optical fiber through which the light passed through the gas detection cell is propagated, and a photodetector which conducts a photoelectric conversion of the light propagated through the optical fiber. Here, the gas detection cell is filled with a measured gas, where a light component with a specific wavelength depending on the gas type is absorbed by the gas.

The photoelectric-converted light is then supplied to an alarm system. Since an input signal to the alarm system indicates a characteristic corresponding to a specific wavelength that is absorbed by the gas in the gas detection dell, the alarm system can detect the gas or identify the gas type by monitoring the absorption characteristic, whereby it alarms depending on circumstances. In this case, a wavelength of the light emitted from the laser light source can be set to correspond to the absorption spectrum of a measured gas to detect only the specific gas type.

However, in the conventional system, detectable gas types are limited to those which have absorption spectra in a wavelength band(near infrared region) where a light can be propagated at a low loss in the propagation optical fibers. On the other hand, for the purpose of detecting many types of gas, a plurality of laser light sources need to be prepared depending on the number of wavelengths that correspond to the respective gas absorption spectra or a particular device such as a wavelength-variable laser is required. Therefore, the system will be very costly.

Meanwhile, most of air-polluting substances such as CO, NO2 or explosive gases such as propane have absorption spectra that are located in a sub-millimeter wave band to a far infrared region rather than the near infrared region. Since there is no optical fiber that can waveguide a light with such a wavelength, the conventional optical fiber remote sensing system cannot detect a gas with an absorption spectrum that is located in a micro wave band to a sub-millimeter wave band.

Though an electromagnetic-wave oscillator for such a wave band can be used to monitor the gas absorption in the micro wave band to sub-millimeter wave band, such oscillators are very difficult to produce and are costly. Namely, it is impractical to dispose a plurality of such costly oscillators at a place where a gas leakage is monitored. Besides, since the oscillation frequency of the sub-millimeter wave band oscillators is generally fixed within a narrow range, gas types detectable by them will be limited.

SUMMARY OF THE INVENTION

Accordingly, it is an object of the invention to provide an optical fiber remote sensing system by which a measured substance with an absorption spectrum from micro wave band to sub-millimeter wave band can be detected.

It is a further object of the invention to provide an optical fiber remote sensing system which can be composed at a low cost and with a compact size.

It is a still further object of the invention to provide an optical fiber remote sensing system in which various types of measured substances can be detected.

According to the invention, an optical fiber remote sensing system, comprises:

first and second light sources which are connected to ends of branched optical fibers and emit lights with two wavelengths different from each other;

one or more photodetectors which conduct a photoelectric conversion of the lights propagated through the optical fibers from the first and second light sources and generate an electromagnetic wave with a wavelength corresponding to a difference between the two different wavelengths; and a measuring means which receives the electromagnetic wave propagated through a measured substance and measures a state of the measured substance based on an optical absorption characteristic of the measured substance.

BRIEF DESCRIPTION OF THE DRAWINGS

The invention will be explained in more detail in conjunction with the appended drawings, wherein.

DESCRIPTION OF THE PREFERRED EMBODIMENTS

Before explaining an optical fiber remote sensing system in the preferred embodiments, the aforementioned conventional optical fiber remote sensing system will be explained in FIG. 1.

Figure 1:
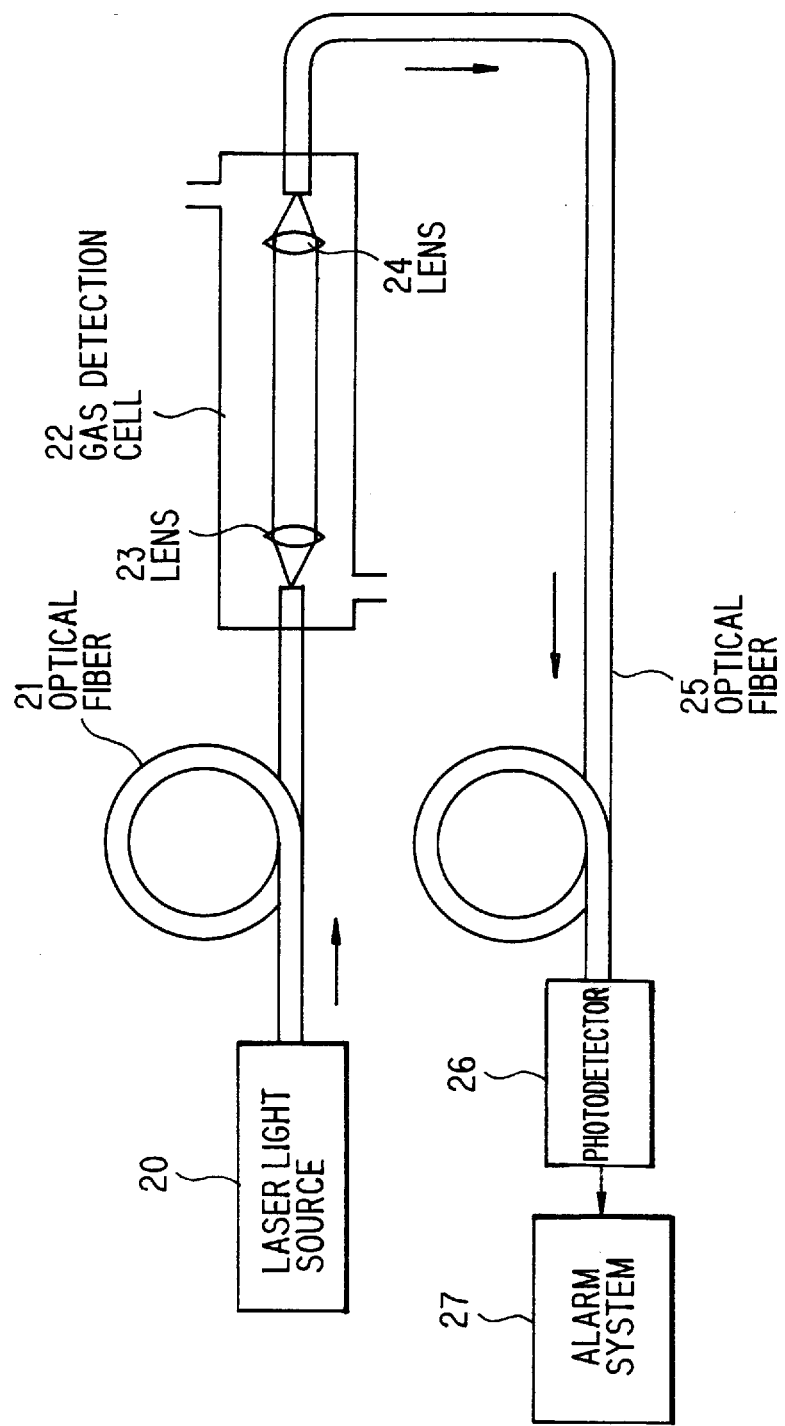
FIG. 1 shows the composition of a conventional optical fiber remote sensing system.

FIG. 1 shows the composition of a conventional optical fiber remote sensing system. In this optical fiber remote sensing system, a light in near infrared region or visible region which is emitted from a laser light source 20 is propagated at a low loss through an optical fiber 21 and is led to a gas detection cell 22 located at a measuring point. The gas detection cell 22, which is provided with lenses 23, 24 opposite to each other, is filled with a measured gas. When the light from the optical fiber 21 is passed through the gas, a light component with a specific wavelength depending on the gas type is absorbed by the gas.

The light passed through the gas detection cell 22 is propagated through an optical fiber 25, supplied to a photodetector 26, where it is photoelectric-converted, then supplied to an alarm system 27. Since an input signal to the alarm system 27 indicates a characteristic corresponding to a specific wavelength that is absorbed by the gas in the gas detection dell 22, the alarm system 27 can detect the gas or identify the gas type by monitoring the absorption characteristic, whereby it alarms depending on circumstances. In this case, a wavelength of the light emitted from the laser light source 20 can be set to correspond to the absorption spectrum of a measured gas to detect only the specific type of gas.

Figure 2A:
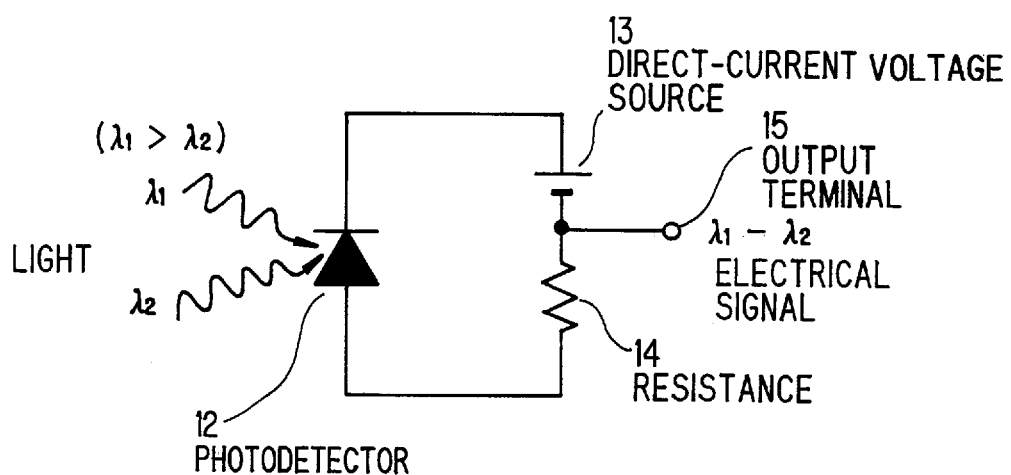
FIGS. 2A and 2B show the theoretical composition of an optical fiber remote sensing system of the invention.

Next, the principle of the invention, by which an electromagnetic wave such as a millimeter wave and a sub-millimeter wave can be substantially propagated in an optical fiber, will be explained in FIGS. 2A and 2B. As shown in FIG. 2A, in a series circuit which comprises a photodetector 12 such as a photodiode, a direct-current voltage source 13 and a resistance 14, when two lights with different wavelengths $\lambda 1$, $\lambda 2 (\lambda 1 > \lambda 2)$ are supplied onto the photodetector 12, there occurs an electromagnetic wave (electrical signal) with a wavelength corresponding to the wavelength difference($\lambda 1 - \lambda 2$) between the two lights due to the square-law detection characteristic of the photodetector 12. The electromagnetic wave occurred can be output from the connection point of the direct-current voltage source 13 and the resistance 14 to an output terminal 15(heterodyne detection).

The wavelength of the electromagnetic wave is determined by the difference of the wavelengths $\lambda 1$, $\lambda 2$ of the two lights to be supplied, whereby an electromagnetic wave in a micro wave band, millimeter wave band and sub-millimeter wave band can be easily produced. For example, to produce a sub-millimeter wave with 1 THz wavelength, two optical wavelengths need to be 1.550 $\mu$m and 1.558 $\mu$m, which can be easily obtained by using semiconductor laser light sources.

Figure 2B:
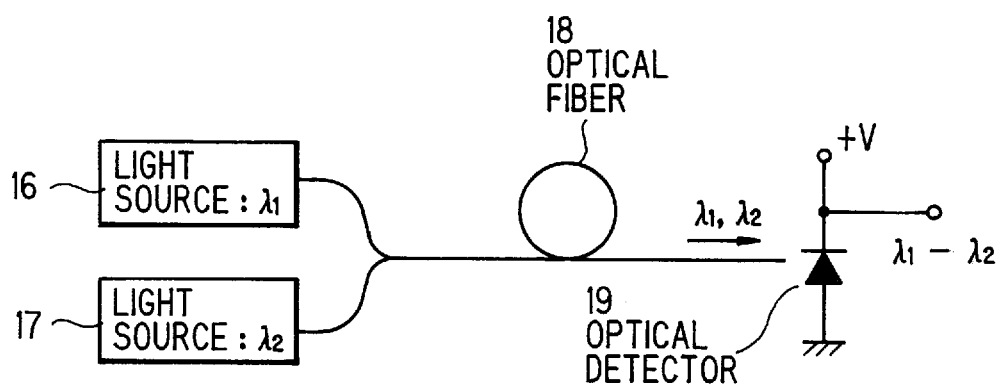

Also, as shown in FIG. 2B, by guiding two light with wavelengths $\lambda 1$, $\lambda 2$ emitted from light sources 16, 17 through an optical fiber 18 to a measurement point and supplying the lights to a photodetector 19 and synthesizing them at the measurement point, an electromagnetic wave (electrical signal) with sub-millimeter wavelength can be obtained from the photodetector 19. Namely, by using this manner, the electromagnetic wave with sub-millimeter wavelength, which cannot be propagated in an optical fiber, can be brought as if it were propagated through an optical fiber to the measurement point.

Furthermore, by tuning an oscillation wavelength of one of the light sources 16, 17 by changing a current or temperature, a wavelength of the electromagnetic wave obtained can be wide varied from a micro wave band to a millimeter wave band or sub-millimeter wave band. Therefore, many types of gases can be detected, and a gas type to be detected can be quickly changed.

As explained above, in this invention, by mixing two lights with different wavelengths in an optical detector, there are occurred an electromagnetic wave with a wavelength that corresponds to the wavelength difference between the two lights(an electrical signal with a frequency corresponding to the wavelength difference). The electromagnetic wave can be provided with a wavelength in the wide range from a micro wave band to a millimeter wave band or sub-millimeter. The electromagnetic wave is used to detect and identify a specific gas in the air by utilizing an optical absorption characteristic of the specific gas.

Next, an optical fiber remote sensing system in the preferred embodiment will be explained in FIG. 3.

Figure 3:
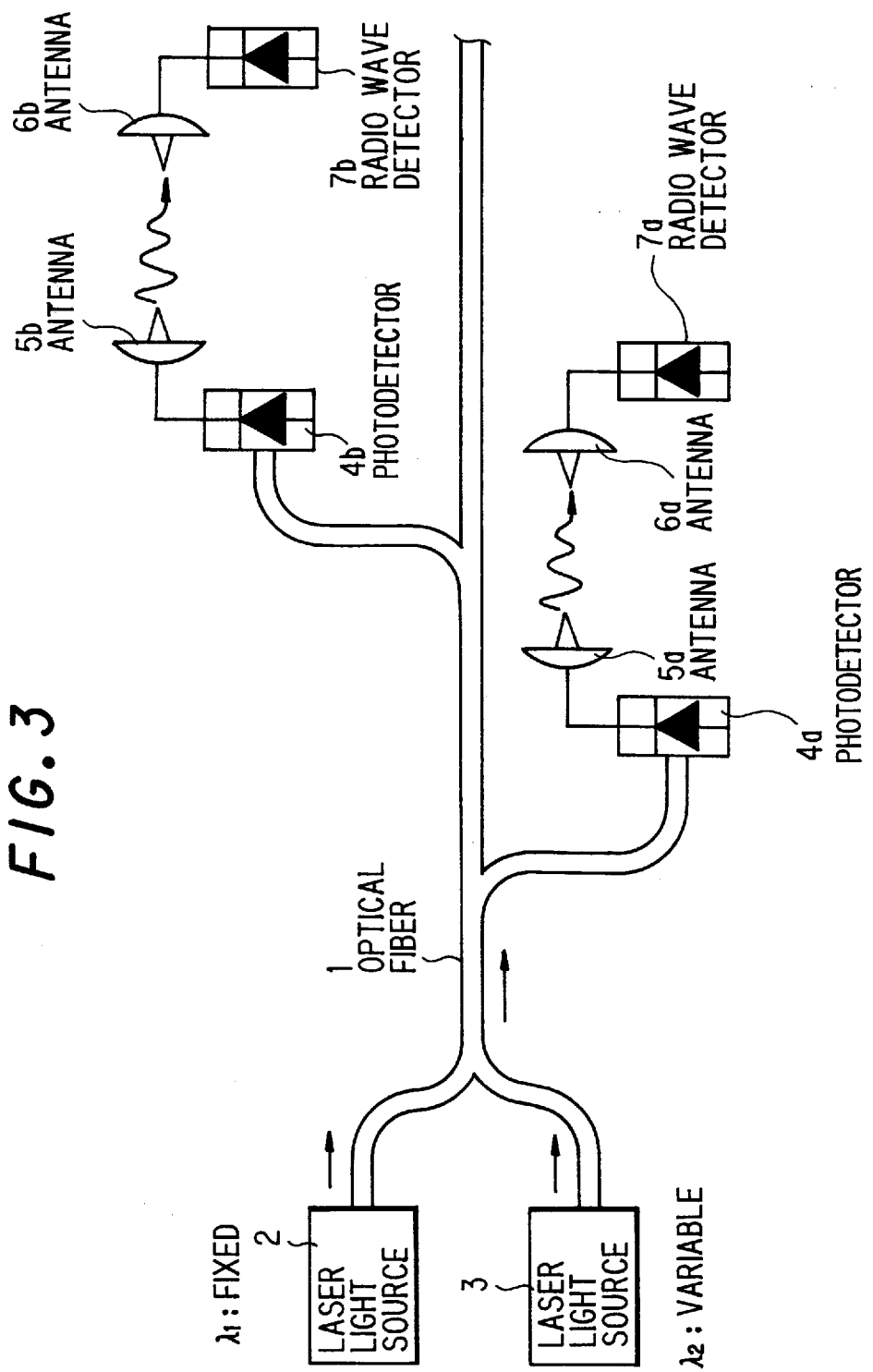
FIG. 3 shows the composition of an optical fiber remote sensing system in a preferred embodiment according to invention.

As shown in FIG. 3, the optical fiber remote sensing system comprises laser light sources 2, 3 with different oscillation wavelengths $\lambda 1$, $\lambda 2$ which are connected with one end of an optical fiber 1, optical detectors 4a, 4b which are connected with the other end of the optical fiber 1 or with a branch of the optical fiber 1, antennas 5a, 5b, 6a, 6b and radio wave detectors 7a, 7b, to give a detection system for toxic gas and dangerous gas.

The optical fiber 1 to be used is a standard single-mode quartz fiber. As the laser light sources 2, 3, for example, a distributed feedback(DFB) laser is suitable because it is compact and easy to handle. Of the laser light sources 2, 3, the laser light source 2 has a fixed oscillation wavelength of $\lambda 1$ and the laser light source 3 has a variable oscillation wavelength of $\lambda 2$. Therefore, the wavelength of an electromagnetic wave obtained by the optical detectors 4a, 4b explained later can be wide varied from a micro wave band to a millimeter wave band or sub-millimeter, thereby detecting many types of gases and quickly changing a gas type to be detected.

The oscillation wavelength of a DFB laser used as the laser light source 3 can be easily changed by varying an injection current or temperature. It is desirable to use it after the wavelength stabilization by a conventional method. The oscillation wavelengths $\lambda 1$, $\lambda 2$ can be in either of 1.3 $\mu$m band and 1.5 $\mu$m band.

Alternatively, a visible region laser or a AlGaAs short-wavelength laser may be used in combination with an plastic optical fiber. For the purpose of guiding the lights from the laser light sources 2, 3 to the optical fiber 1 or branching the optical fiber 1 into two optical fibers, optical fiber couplers can be used. As the optical detectors 4a, 4b, broad band photodiodes can be used. Alternatively, a heterojunction FET(HJ-FET or HEMT), a Schottky-junction field-effect transistor(MESFET), a hetero-bipolar transistor(HBT) etc. may be used. For example, it is proved that a difference frequency signal can be obtained by supplying lights with different wavelengths to a gate of HJ-FET.

In operation, laser lights with, e.g., near infrared region wavelengths $\lambda 1$, $\lambda 2$ that can be propagated by an 1.3 $\mu$m band or 1.55 $\mu$m band optical fiber, which are emitted from the laser light sources 2, 3., are led through the optical fiber 1 to the optical detectors 4a, 4b, where they are heterodyne-detected and converted into an electromagnetic wave (difference frequency signal) corresponding to a wavelength in micro wave band or millimeter wave band that is equal to the wavelength difference between $\lambda 1$ and $\lambda 2$.

The micro wave band or millimeter wave band signal obtained by the photodetector 4a or 4b is amplified up to a proper level(or without amplifying if a sufficient output level is obtained), then guided to first antennas 5a, 5b, therefrom radiated into the air as an radio wave, then received by second antennas 6a, 6b opposite to the first antennas 5a, 5b, respectively. As the antennas 5a, 5b, 6a and 6b, for example, a parabolic antenna, which has a high directivity, is suitably used. The distances between the antennas 5a and 6a and between the antennas 5b and 6b are, for example, 30 cm to several meters.

From the micro wave band or millimeter wave band signal received by the antennas 6a, 6b, its signal intensity etc. is detected by the radio wave detectors 7a, 7b. As the radio wave detectors 7a, 7b, for example, a Schottky diode is used. A specific wavelength band of the radio wave received by the antennas 6a, 6b is absorbed depending on a type of gas which exists in the radio wave propagation space between the antennas 5a, 6a or between the antennas 5b, 6b. Therefore, by monitoring the signal intensity of the electromagnetic wave received by the radio wave detectors 7a, 7b, the type and state of the gas existing in the radio wave propagation space between the antennas 5a, 6a or between the antennas 5b, 6b can be measured.

In this embodiment, the radio wave, which propagates through the space between the antennas 5a, 6a or between the antennas 5b, 6b, belongs to the range from a micro wave band to a sub-millimeter wave band. Therefore, air-polluting substances such as CO, NO2 and explosive gases such as propane, most of which have many absorption spectra in sub-millimeter wave band to far infrared region that cannot be detected by the conventional optical fiber remote sensing system, can be detected without using a costly electromagnetic wave oscillator for micro wave band to sub-millimeter wave band.

For reference, the absorption characteristics of gaseous substances that have absorption spectra in millimeter wave band to sub-millimeter wave band are shown below(M. Uetaki, "Millimeter Wave Technique Manual and Development", issued by Realize Co., p.156).

TABLE

| Measured Gas | Milli-W.B. | 200 GHz Band | 270 GHz Band | 560 GHz Band | 640 GHz Band | Sub-Milli W.B. | Characteristic of Gas |
|---|---|---|---|---|---|---|---|
| ozone (O3) | | 206.132 | 276.923 | 566.294 | 647.840 | | a space suit for guarding the globe |
| chlorine monoxide (ClO) | | 204.35 | 278.63 | 575.39 | 649.45 | | ozone layer breaking substance, derived from Freon |
| chlorine dioxide (ClO2) | | | | | 624.269 | | ozone layer breaking substance, derived from Freon |
| hypochloric acid (HOCl) | | 202.485 | 270.832 | 555.697 | 648.618 | | ozone layer breaking factor, reservoir molecule |
| hydrogen chloride (HCl) | | | | | 625.916 | | ozone layer breaking factor, reservoir molecule |
| bromine monoxide (BrO) | | | | 576.31 | 627.36 | | ozone layer breaking substance, derived from CH3Br |
| hydrogen bromide (HBr) | | | | 500.647 | | | ozone layer breaking factor, reservoir molecule |
| hydrogen fluoride (HF) | | | | | | 1,232.48 | derived from Freon |
| steam (H2O) | 183.310 | | | 556.936 | | | atmospheric component earth-warming gas |
| hydroxyl group (OH) | | | | | | 2,513.0 | ozone dissociation factor |
| hydroperoxyl (HO2) | | | 265.770 | 569.390 | 625.660 | | ozone dissociation factor |
| hydrogen peroxide (H2O2) | | 204.575 | 270.610 | 555.643 | 647.026 | | reservoir molecule |
| nitrogen monoxide (NO) | | | 250.437 | 551.188 | 651.433 | | ozone dissociation factor derived from N2O |
| nitrogen dioxide (NO2) | | | 274.96 | 578.2 | 647.9 | | ozone dissociation factor derived from N2O |
| nitrous oxide (N2O) | | 200.975 | 276.328 | 577.575 | 627.748 | | derived from organic fertilizer, earth-warming gas |
| nitric acid (HNO3) | | | 269.210 | 544.350 | 647.759 | | reservoir molecule |
| hydrogen cyanide (HCN) | | | 265.886 | | 620.304 | | photochemical reaction factor in middle atm. |
| carbon monoxide (CO) | | 230.538 | | 576.268 | | | derived from human production activities |
| formaldehyde (H2CO) | | | | 561.900 | 647.085 | | photochemical reaction factor in upper atm. |
| sulfur dioxide (SO2) | | 203.391 | 267.719 | 559.500 | 641.825 | | stratosphere aerosol formation |
| carbonyl sulfide (OCS) | | 206.745 | 267.530 | 558.990 | 643.863 | | a sulfur carrier to upper layer |
| temperature/ barometric pressure (O2) | 60/118 | | | | | | basic physical quantities to determine atmospheric state |

As seen from the above table, for example, in case of detecting NO which is a component of car exhaust gas, frequencies of 250.437 GHz and 551.188 can be used. Also, in case of detecting HF which is derived from Freon®, a sub-millimeter wave band frequency of 1,232.48 GHz can be used.

Though this embodiment is concerned to the gas detection system for toxic gas, dangerous gas etc, an optical fiber remote sensing system of the invention can be wide applied to environmental pollution monitoring systems and meteorology monitoring systems. For example, it can be used for the monitoring of a liquid(water analysis) in addition to gases, meteorological observations by which an occurrence of mist on the road and a rainfall state are remotely monitored, and astronomical observations.

Although the invention has been described with respect to specific embodiment for complete and clear disclosure, the appended claims are not to be thus limited but are to be construed as embodying all modification and alternative constructions that may be occurred to one skilled in the art which fairly fall within the basic teaching here is set forth.

What is claimed is:

1. An optical fiber remote sensing system, comprising:

first and second light sources which are connected to ends of branched optical fibers and emit lights with two wavelengths different from each other;

one or more optical detectors which conduct a photoelectric conversion of said lights propagated through said optical fibers from said first and second light sources and generate an electromagnetic wave with a wavelength corresponding to a difference between said two different wavelengths; and a measuring means which receives said electromagnetic wave propagated through a measured substance and measures a state of said measured substance based on an optical absorption characteristic of said measured substance.

2. An optical fiber remote sensing system, according to claim 1, wherein:

said measured substance is a gas, and said measuring means detects a state and a type of said gas based on an electrical signal output from a radio wave detector which receives said electromagnetic wave propagated through said gas, by using said optical absorption characteristic that only a specific wavelength of said electromagnetic wave is absorbed by said gas when said electromagnetic wave is propagated through said gas.

3. An optical fiber remote sensing system, according to claim 2, wherein:

said specific wavelength belongs to a range from a micro wave band to a millimeter wave band or a sub-millimeter wave band.

4. An optical fiber remote sensing system, according to claim 2, wherein:

said measuring means comprises a first antenna which radiates an electrical signal which corresponds to said electromagnetic wave output from said optical detectors as a radio wave into the air, a second antenna which receives said radio wave, and said radio wave detector which detects said state and type of said gas which is located between said first and second antennas, based on an electrical signal output from said second antenna.

5. An optical fiber remote sensing system, according to claim 1, wherein:

at least one of said first and second light sources is of a wavelength-variable type.

* * * * *